United States Patent [19]
Maget et al.

[11] Patent Number: 6,010,317
[45] Date of Patent: Jan. 4, 2000

[54] ELECTROCHEMICAL CELL MODULE HAVING AN INNER AND AN OUTER SHELL WITH A NESTED ARRANGEMENT

[75] Inventors: Henri J. R. Maget, La Jolla; Robert J. Rosati, Carlsbad, both of Calif.

[73] Assignee: Baxter International Inc., Deerfield, Ill.

[21] Appl. No.: 09/144,910

[22] Filed: Sep. 1, 1998

[51] Int. Cl.[7] ............................... F04B 17/00; C25B 9/00
[52] U.S. Cl. ..................... 417/379; 204/283; 204/266; 204/228
[58] Field of Search ................... 417/379, 390; 204/283, 266, 204, 252

[56] References Cited

U.S. PATENT DOCUMENTS

| | | | |
|---|---|---|---|
| 4,210,501 | 7/1980 | Dempsey et al. | 205/620 |
| 4,276,146 | 6/1981 | Coker et al. | 204/266 |
| 4,488,951 | 12/1984 | Nolan et al. | 205/629 |
| 4,617,101 | 10/1986 | Sato et al. | 204/252 |
| 4,648,955 | 3/1987 | Maget | 204/258 |
| 4,687,423 | 8/1987 | Maget et al. | 417/379 |
| 4,902,278 | 2/1990 | Maget et al. | 604/132 |
| 5,149,413 | 9/1992 | Maget | 204/258 |
| 5,454,922 | 10/1995 | Joshi et al. | 204/265 |
| 5,593,552 | 1/1997 | Joshi et al. | 204/228 |

*Primary Examiner*—Charles G. Freay
*Assistant Examiner*—Robert Z. Evora
*Attorney, Agent, or Firm*—Brown, Martin, Haller & McClain, LLP

[57] ABSTRACT

An electrochemical cell module has an outer shell of conductive material defining a cavity, an electrolytic membrane located in the cavity, first and second pervious electrodes located on opposite sides of the membrane, and a seal member located between the second electrode and the outer shell. Contacts for connecting a power source across the electrodes are provided on the second electrode and on the outer shell on the same side of the membrane as the second electrode, and the outer shell provides a current collector for the first electrode without requiring any external leads across the module.

15 Claims, 3 Drawing Sheets

ELECTROCHEMICAL CELL MODULE HAVING AN INNER AND AN OUTER SHELL WITH A NESTED ARRANGEMENT

CROSS-REFERENCES TO RELATED APPLICATIONS

The present application is related to application Ser. No. 08/924,564 filed Sep. 5, 1997, entitled "Electrochemical Syringe Pump".

BACKGROUND OF THE INVENTION

The present invention relates generally to electrochemical cell devices or modules.

An electrochemical cell is typically formed by positioning an electrolyte between and in contact with a cathode and an anode. In some cases, the electrolyte is an electrolytic membrane. Such a cell may be configured in a fuel cell to generate electricity, or in an electrochemical pumping module to do mechanical work. In the latter case, an electrical voltage is applied across the anode and cathode, and gas is generated by the cell to apply external gas pressure in a pumping action. Electrochemical pumps of this type are used in devices for dispensing liquids or fluids in a controlled manner, for example medications, fragrances, and the like. The external gas pressure produced by the cell in some of these cases is applied to a flexible barrier or membrane to force liquid out of an adjacent liquid chamber at a controlled flow rate.

One such fluid delivery device is described in U.S. Pat. No. 4,902,278 of Maget entitled "Fluid Delivery Micropump". In some other cases, the gas pressure is used to move a syringe plunger and this dispenses a fluid, as described in application Ser. No. 08/924,564 referred to above.

In prior art electrochemical modules, the electrolytic membrane, the electrodes and the current collectors are secured together in a sandwich-like assembly. The components are stacked in a flat, parallel arrangement and axially compressed by means of a bolted end plate. In prior art fluid delivery devices (U.S. Pat. No. 4,902,278), the stacked assembly also includes a battery in direct contact with the air cathode. In this instance, an external electrical connection is required to connect the battery to the other electrode on the other side of the electrolytic membrane or ionomer, i.e. the side producing the gas pressure. The requirement for an external lead is a problem in mounting and sealing the electrochemical cell module in a suitable fluid delivery device housing. The external lead also produces problems when scaling up of the small electrochemical cell module to large devices, and in volume manufacture of the modules.

SUMMARY OF THE INVENTION

It is an object of the present invention to provide a new and improved electrochemical cell module for use in liquid dispensing devices and the like.

According to the present invention, an electrochemical cell module or assembly is provided, which comprises an outer shell of conductive material defining a cavity having a first end and a second end, an electrolytic membrane located in the cavity adjacent the first end of the cavity, first and second pervious electrodes located on opposite sides of the membrane so as to contact the membrane, the first electrode being located at the first end of the cavity, and a seal member between the second electrode and the outer shell. A power supply may be connected between the second electrode and the conductive shell to apply an electrical voltage to the electrodes, the conductive shell acting as the current collector for the first electrode.

In this arrangement, there is no need for an external lead extending around the outside of the electrochemical cell to connect the first electrode to the power supply or battery, since the outer shell itself forms the current collector or connection from the battery to the electrode. In a preferred embodiment of the invention, the outer shell or first current collector forms the first end of the cavity. A gas pervious disc may either be formed integrally with the outer shell or suitably secured across a first, open end of the shell and in electrical contact with the conductive shell. This arrangement allows the contacts for the two electrodes to the battery to be made on the same side of the ion exchange membrane, avoiding the need for external wires or the like. The module components can also be sealed readily with this arrangement, whereas modules with external wires were often unsealable.

Preferably, the module includes an inner shell nesting inside the outer shell, the inner and outer shells each having gas-pervious disc-shaped end portions between which the electrolytic membrane and electrodes are sandwiched. The shells are of conductive material and form current collectors for the respective electrodes. Each disc-shaped end portion preferably has a plurality of corrugations extending across its surface, with the corrugations on one end portion arranged at an angle to those on the other end portion. The end portions of each current collector each have a plurality of openings for gas flow to and from the electrodes. This allows for numerous point contacts across the electrodes while still permitting gas flow through the current collectors. The corrugations allow increased structural stiffness and promote heat conduction. At the same time, the cell current is not impaired. The cell current is dependent on mass transfer from the gas phase (air) to the electrode surface and on the transverse (current collector to electrode) and longitudinal (electrode resistance between current collector contact points) resistances. The corrugated current collector structure along with the multiple openings in the electrode ensures that oxygen from the air is readily available at the electrode surface.

The seal between the outer shell and the second electrode has three functions. First, it electrically insulates the first current collector from the second current collector. Secondly, it prevents loss of pressurized gas or oxygen released from the first electrode to the second electrode, which is exposed to ambient air. Thirdly, it preloads the shells to ensure contact between the electrodes and current collectors. Preferably, the second electrode is in contact with one end of an inner, annular shell of conductive material, and the seal comprises an annular ring seal member compressed between the inner and outer shells in a nested arrangement. A radial type seal will provide a better seal to the membrane than a face seal in the structure, which would be liable to deform during manufacture. The outer shell preferably has a smooth outer surface for ready sealing to an external sealing member.

In this module or assembly, the inner and outer shells act as both the current collectors for supplying current to the electrodes, and as the support for the respective electrodes and the electrolytic membrane. The outer shell also acts as the modular housing of the electrochemical cell module.

The electrochemical cell module of this invention provides a low cost, modular, scalable assembly of two nested conductive shells which sandwich a resilient seal and an electrolytic membrane while allowing connection of both electrodes to a power source on the ambient air side of the module. The electrochemical cell module can be readily used for insertion, as a unitary component, into a holding structure while simultaneously establishing electrical contacts to the electrodes at one end of the module. The module can be readily machine-assembled.

BRIEF DESCRIPTION OF THE DRAWINGS

The invention will be better understood from the following detailed description of some preferred embodiments of the invention, taken in conjunction with the accompanying drawings, in which like reference numerals refer to like parts, and in which.

DESCRIPTION OF THE PREFERRED EMBODIMENTS

Figure 1:
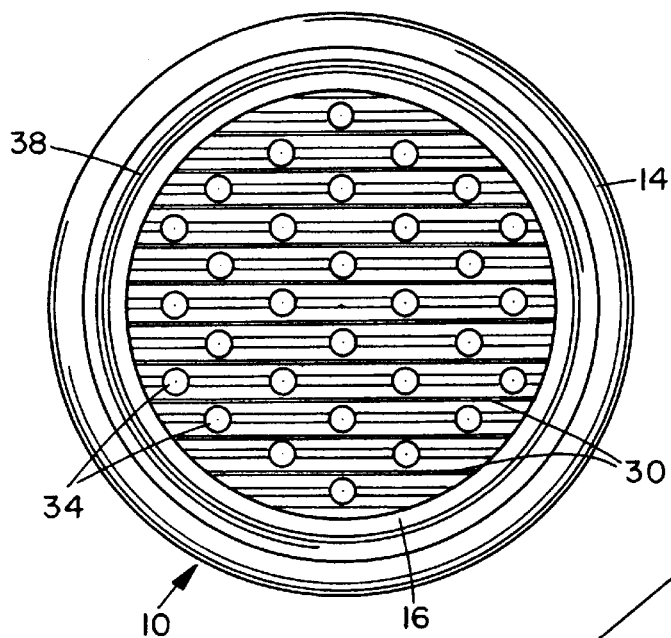
FIG. 1 is a top plan view of an electrochemical cell module according to a first embodiment of the invention.
Figure 2:
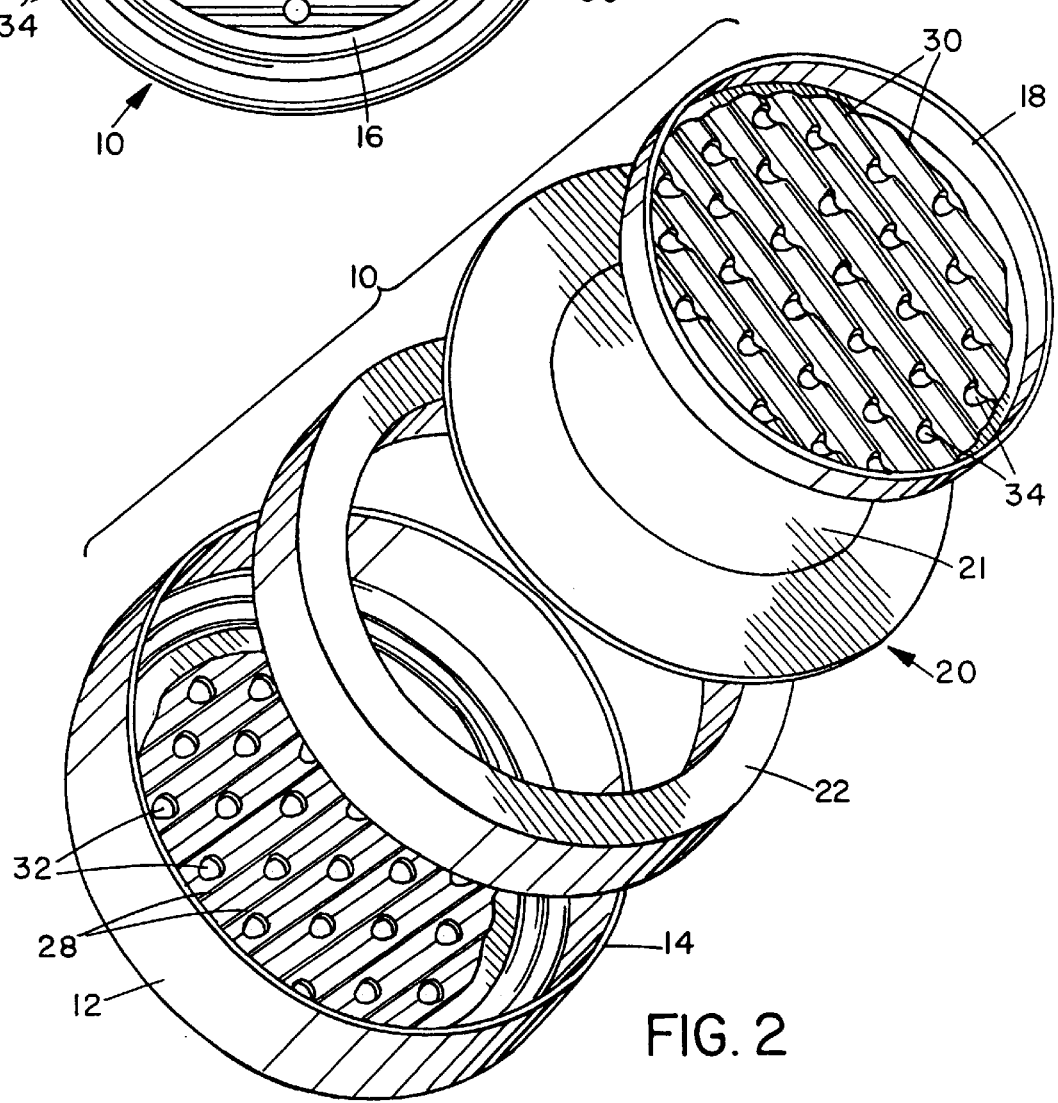
FIG. 2 is an enlarged perspective view of the components of the electrochemical cell module before assembly.
Figure 3:
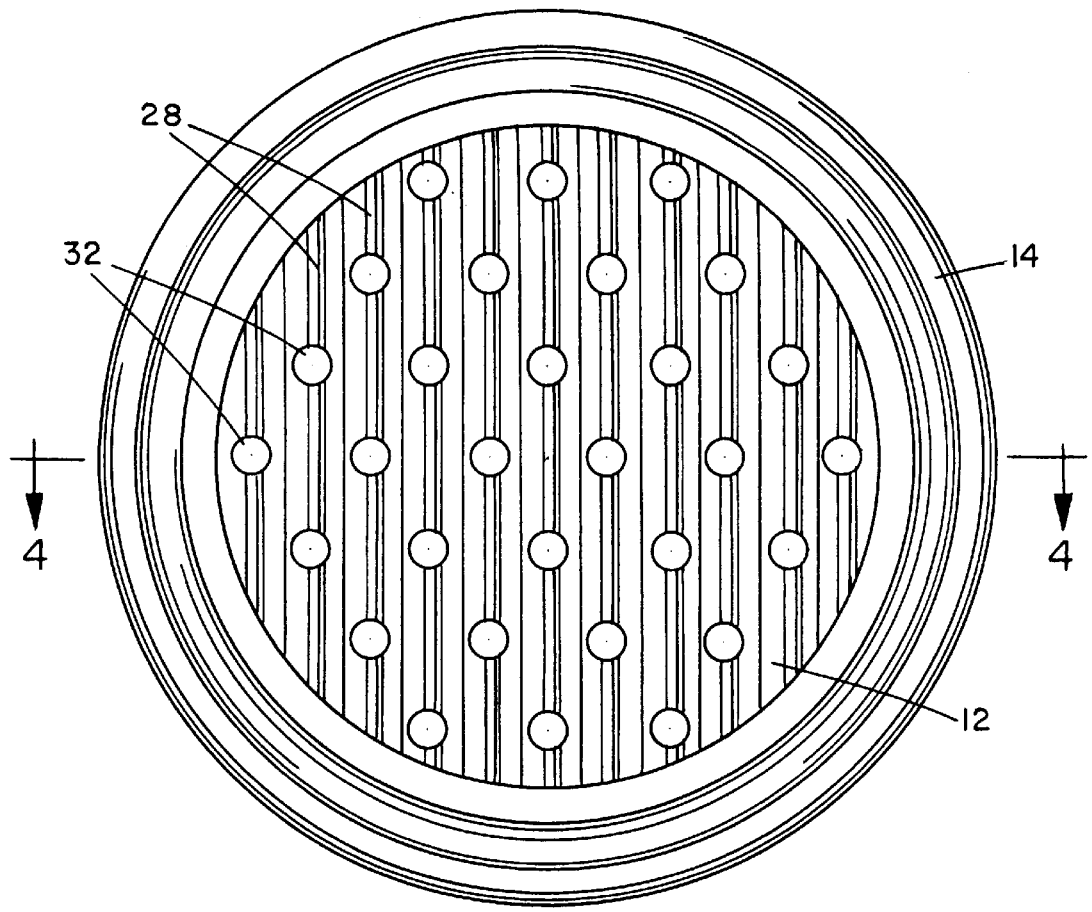
FIG. 3 is an enlarged bottom plan view of the module.
Figure 4:
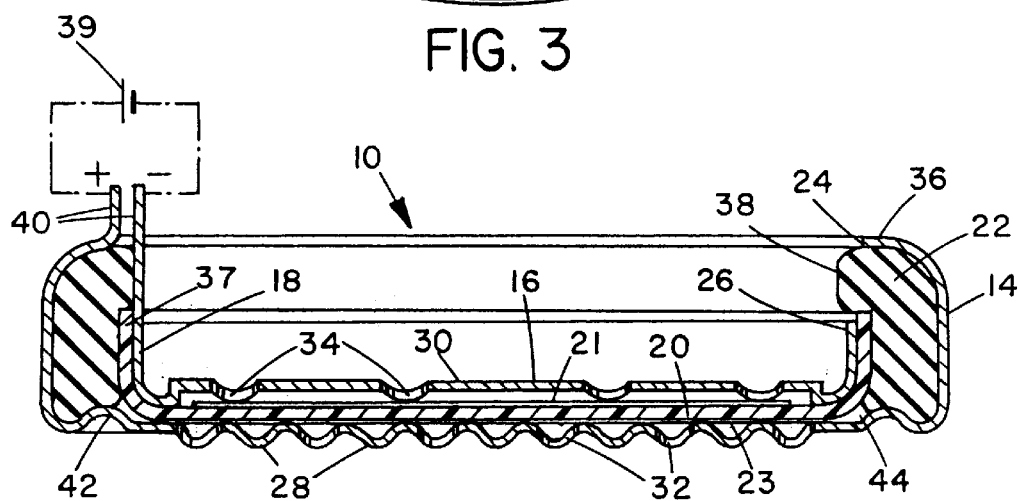
FIG. 4 is a sectional view taken on line 4—4 of FIG. 3.

FIGS. 1 to 5 illustrate an electrochemical cell module or assembly 10 according to a first embodiment of the present invention. The module comprises four basic parts, as best illustrated in FIG. 2, in which the parts are shown separated prior to assembly. The module parts are a first current collector 12 mounted at one end of an outer shell 14, a second current collector 16 mounted at one end of an inner shell 18, an ion exchange electrochemical cell 20 sandwiched between the current collectors, and a ring seal member 22. The electrochemical cell comprises an electrolytic membrane with electrodes 21, 23 formed integrally on opposite sides of the membrane. The electrodes comprise electro-catalytically active surfaces attached to opposite sides of the membrane. Each electrode is of smaller diameter than the membrane, as illustrated in FIGS. 2 and 4. The seal member 22 is located between the outer shell 14 and an upstanding rim portion 37 of the electrolytic membrane when the parts are assembled, as best illustrated in FIG. 4.

The shells 14,18 are each made of a suitable conductive material, and are generally ring shaped with a first, open end 24,26, respectively, and a second end across which the respective current collector 12,16 is mounted. The current collectors may be formed integrally with the respective shells, as illustrated, or may be formed separately and suitably secured in an end opening of the shell by adhesive, pressure contact or the like. Each current collector is preferably formed with a plurality of spaced, parallel corrugations 28, 30, respectively, across its surface, and the shells are assembled such that the corrugations 28 on one current collector are at an angle to the corrugations 30 on the other current collector. Each current collector also has a plurality of openings 32,34, respectively, across its surface, preferably located in the troughs of the corrugated face which faces the electrolytic membrane 20, to ensure that the uninterrupted rounded peaks of the corrugations contact the membrane. The electrolytic membrane is pinched between opposing corrugations at each point where the corrugations cross one another, providing smooth, continuous pinching surfaces only, and reducing the risk of assembly damage.

The shells 14, 18 may be of shapes other than cylindrical, although cylindrical shapes are preferred for ease of sealing and assembly. The shells may be of materials having sufficient compliance to compensate for membrane thickness changes under varying moisture conditions. In this case, seal member 22 will not be needed.

The use of a plurality of corrugations across each current collector to provide opposing contacts on the electrodes at each point where the opposing corrugations cross one another provides good electrical point contacts while still permitting the desired gas flow through each current collector. Preferably, the contact spacing is such that resistive losses are considerably reduced. The plates may be positioned with the corrugations at any relative angle to one another. The ratio of hole space to contact space is critical and may be optimized to a particular application. The contact space is made as close as possible while still providing sufficient space for the required gas flow openings, depending on the required flow rate.

In order to assemble the module, the seal 22, electrochemical cell 20, and then the inner shell 18 are placed into the cavity formed by the outer shell 14, sandwiching the seal and membrane 20 between the inner and outer shells. The outer shell 14 and seal 22 are each of height greater than that of the inner shell, and the open end of the outer shell is then crimped or bent inwardly to form an inturned rim 36, simultaneously forming an inturned rim 38 of the seal 22 and securing the seal 22, membrane 20, and inner shell 18 within the outer shell. The electrolytic membrane 20 is also formed into a cup-like shape with an upstanding rim or wall 37 between the inner shell and the seal 22, as best illustrated in FIG. 4.

The crimped outer shell and inner shell hold the parts together, and also form contact points on the same side of the electrochemical cell for connecting a remote power source 39 to the electrodes via suitable contact pins or tabs 40. Alternatively, a battery (not illustrated) may be seated in the inner shell to directly contact both the inner and outer shells on the negative and positive sides, respectively, of the battery. Suitable electrical contacts are provided between the crimped rim 36 of the outer shell and one battery terminal, and between the inner shell 18 and the other battery terminal, so as to provide a voltage across the electrodes. Any suitable electrical contact may be provided to either a seated battery or to a remote power source, such as spring-loaded contact pins, welding, soldering, and the like. The advantage of the inner and outer nested shell arrangement is that contacts for both electrodes can be provided on the same side of the electrochemical cell module, eliminating the requirement for any electrical leads extending around the outside of the cell from one side to the other.

An annular groove 42 is preferably formed on the lower end of the outer shell surrounding current collector 12. This compensates for any non-parallel assembly of the inner and outer shells.

Figure 5:
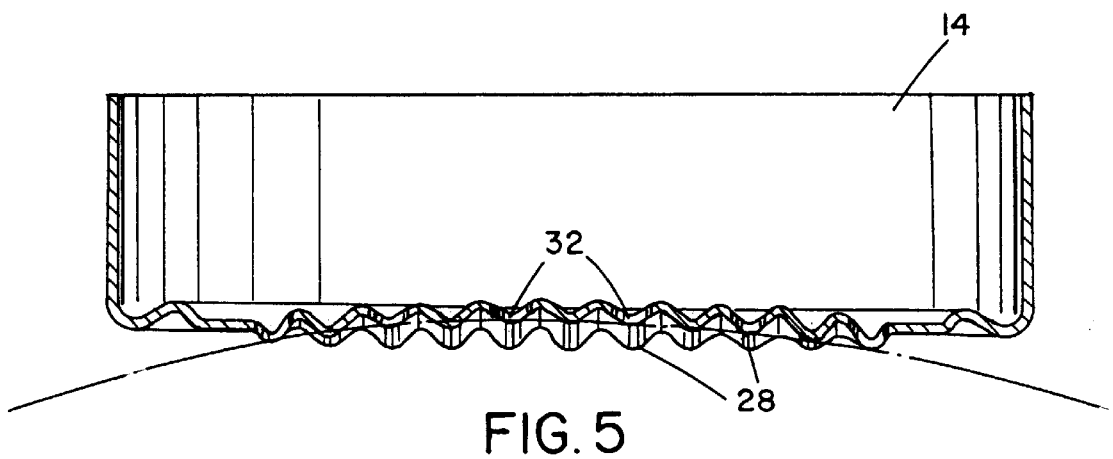
FIG. 5 is a sectional view of the outer shell of the module, showing a domed configuration of the corrugated electrode face.

In a preferred embodiment of the invention, the base or lower end wall of the outer shell 14, including the corrugated current collector 12, is of concave, domed shape prior to assembly, as best illustrated in FIG. 5. This provides a form of pre-loading. When assembled into a modular unit as in FIGS. 4 and 5, the base is forced into a flat configuration, and is therefore biased upwardly against the other parts lying above it. This helps to hold the components together and provides pre-loading of the current pick ups or corrugations against the electrochemical cell.

The outer shell or can 14 is formed with smooth cylindrical outer face and rounded upper and lower edges, allowing the module to be readily inserted into an external seal member.

The shell material is selected depending on the required current to the electrochemical cell, which determines the shell conductivity required. Other considerations in selection of the shell material are the required mechanical strength, chemical stability to the acidic ionomer, resistance to oxidation, electrical resistance to the voltages to be used, formability for forming the required corrugated surfaces, and ability to be processed to form the crimped end sealing the anode from the cathode. Conductive metals satisfying these requirements are titanium, tantalum, zirconium, and certain stainless steels, such as Carpenter 20. Alloys of titanium, tantalum, niobium, and zirconium may also be used. For example, a Ti—Pd alloy containing a nominal 0.2% of Pd has been found to perform satisfactorily. The shells may also be formed of conductive plastic material, such as carbon-filled polyphenylene sulfide or PPS, if the application requires only a low current. A combination of conductive plastic and metal may also be used, with the shells being formed of conductive plastic material and the end walls or current collectors comprising corrugated discs or inserts of any of the metallic materials described above, which may be suitably attached to make electrical contact with the plastic shell.

The choice of seal material is also critical. The seal material must be inert, i.e. be resistant to an acidic electrolytic membrane, be resistant to hydrolysis and be resistant to oxidative degradation, since it will be exposed to pure oxygen according to the reaction described in more detail below. Since the seal rests directly against the electrolytic membrane 20, it must be made of a material which will not poison the membrane or the catalyst. The seal material must also be highly impermeable to oxygen and water vapor and possess sufficient mechanical strength. Suitable materials are polyolefin thermoplastic elastomers with a shore hardness of 75–90, which do not contain additives or extractables, such as sulfur compounds or oil, which would affect the performance of the electrochemical cell. Stabilized Santoprene® elastomer may be used after addition of a filler to hold the oil in the material, since oil oozing must be prevented. Santoprene® is a registered trade mark of Monsanto Corporation of St. Louis, Mo., licensed to Advanced Elastomer Systems, Inc. Other polyolefin materials may alternatively be used.

The electrochemical cell module of this embodiment is pressure tight, with leakage rates not exceeding 0.035 cc/hr for a pressure difference of 14.7 psi applied to a 1 cm² module. This arrangement minimizes the leak routes for gas and can provide a leak rate of less than 0.005 cc/hr for many fluid delivery devices, or a contribution of less than 1% leakage at a fluid flow rate as low as 0.5 ml/hr. The unit is self supporting at operating pressures to about 80 to 90 psi, and may be used at higher operating pressures if a center support is added.

The operation of an electrochemical cell is well understood in the field, and details of the function of such cells are provided. An electrochemical cell comprises an ion exchange membrane and two integral electrodes, one on each side of the membrane. Such cells operate with any reduction/oxidation material that is electrochemically active so as to react at the first electrode to produce ions, which then migrate across the electrolytic membrane 20 and are reconverted at the second electrode to a molecular state, typically in a gaseous form to produce the desired pumping action. In a preferred embodiment of the present invention, the ion exchange membrane 20 is Nafion®, made by E.I. DuPont de Nemours & Co. This is an acidic material which provides a reaction creating oxygen to provide gas pressure for a pumping action, as described in co-pending application Ser. No. 08/924,564 referred to above, the contents of which are incorporated herein by reference.

Details of the structure and function of an electrochemical pumping module are also set out in U.S. Pat. Nos. 4,402,317 and 4,522,698 of Maget, both entitled "ELECTROCHEMICAL PRIME MOVER." The entire disclosures of those patents are incorporated herein by reference and thus need not be extensively repeated here. Suffice it to say that the voltage gradient established across the electrochemical cell reduces an electrochemically active material, such as atmospheric oxygen entering air inlet ports (not illustrated), at the current collector 16, transports hydrogen ions through the electrolytic membrane 20 to the electrode 23, and regenerates the gas molecules of the electrochemically active material (in this case oxygen), which are then evolved through the openings 32 in current collector 12. The gas exiting via openings 32 may be supplied, for example, via a suitable outlet passageway to act on a diaphragm, plunger or the like to supply a controlled flow of a liquid. When the electrochemically active material is atmospheric oxygen or oxygen from some other source, the electrode 23 is conveniently called the oxygen evolution electrode.

One form of gas generating in the electrochemical cell module is characterized by the following equations:

$$\tfrac{1}{2}O_2 \,(\text{Air}) + 2H^+ + 2e^- \rightarrow H_2O \tag{1}$$

$$H_2O \rightarrow \tfrac{1}{2}O_2 + 2H^+ + 2e^- \tag{2}$$

in which:

Reaction (1) occurs at the interface between the material external to electrode 21 and the ion exchange membrane 20; and Reaction (2) occurs at the interface between the ion exchange membrane 20 and the oxygen evolution electrode 23.

There are of course other electrochemical reactions which will generate gases such as hydrogen which can serve to move the liquid through the device. Electrolysis of water can yield either hydrogen or oxygen, as can galvanic cells using metal oxides such as oxides of zinc, nickel, lead and similar metals. A typical example of such a module is disclosed in U.S. Pat. No. 5,242,565 (Winsel). While air, oxygen and hydrogen are the gases most commonly available by conventional electrochemical reactions, the electrochemical cell of this invention is not intended to be limited to generating only to those three. The electrochemical cell module may generate any gas which 1) can be generated by an electrochemical cell which is similar in function to the oxygen cell exemplified above, 2) is inert or substantially non-reactive with the liquid which it is intended to move through the device of this invention, and 3) is inert to the ambient environment surrounding the device and to the users of the device, in that its generation and dispersion does not also involve the use or generation of toxic, hazardous, reactive or incompatible materials in conjunction with the generation of the subject gas.

Atmospheric air may be permitted to enter the upper end of the module in order to initiate the reaction and activate the battery by any suitable mechanism, as will be understood by those skilled in the field. For example, the electrochemical cell module may be assembled into a pump housing of a syringe body as described in co-pending application Ser. No. 08/924,564 referred to above, and may be activated by means of a cap which is rotated in order to rupture a cover for delivery of a charge transfer medium into the cell, at the same time activating the battery or power source.

The electrochemical cell module 10 is of simple and low cost construction, and may be readily incorporated in any desired liquid delivery systems such as a syringe, self-contained medication delivery device, or other controllable liquid dispensing devices. By providing a radial seal between two nested cans or shells of conductive material forming current collectors, the shells having end faces between which the electrochemical cell is sandwiched, axial forces on the membrane are isolated from the radial sealing forces.

The module can be readily machine assembled, and can be easily inserted as a component into a holding structure. By providing both electrical contacts to the electrodes on the same side of the module, the problems of routing external leads are avoided.

The ring seal 22 has three functions. First, it acts to electrically insulate the anode shell from the cathode shell. Secondly, it prevents loss of compressed oxygen generated at the anode side of the cell to the cathode side (i.e., the ambient air). Thirdly, it acts to maintain contact forces.

Figure 6:
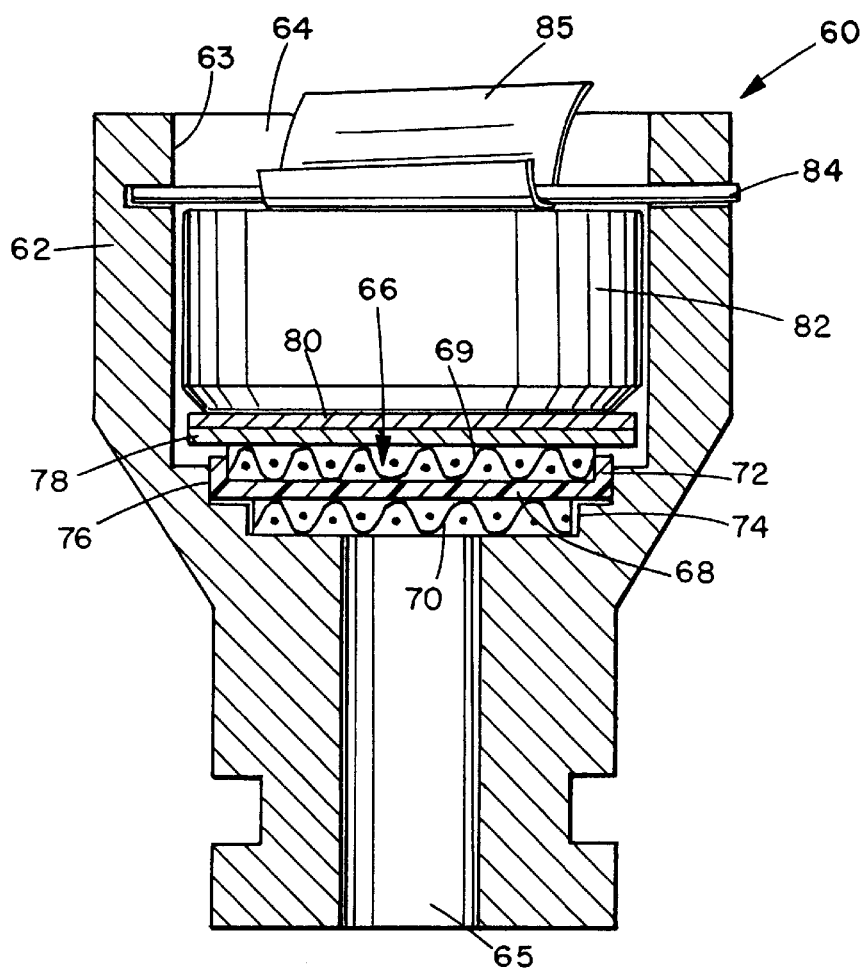
FIG. 6 is a vertical cross-sectional view of an electrochemical pumping module according to a second embodiment of the invention.

FIG. 6 illustrates an electrochemical pumping module 60 according to another embodiment of the invention. In this embodiment, the unit or module basically comprises an outer housing 62 of conductive material having a through bore 63 of stepped diameter extending from inlet end 64 to outlet end 65, and an electrochemical cell 66 which is a press-fit in the stepped portion of through bore 63.

The electrochemical cell 66 basically comprises a membrane 68 of a suitable ion exchange material such as Nafion® with a first current collector 69 on one side of the membrane 68 and a second current collector 70 on the opposite side of the membrane. Each current collector is a rigid, porous metallic disc. The electrolytic membrane is formed into a cup-like shape, with a peripheral rim 72 forming a seat for receiving the first current collector 69 and sealing the current collector from the conductive housing 62. The second current collector 70 is a press-fit in a first stepped diameter portion 74 of the housing through bore, while the peripheral rim 72 of the membrane 68 is designed to be compressed into sealing engagement with an adjacent, larger diameter portion 76 of the through bore, as illustrated. The outer housing is of any suitable conductive material, such as the materials described above for outer shell 14 of the first embodiment, but is preferably of carbon-filled moldable plastic material such as conductive PPS (polyphenylene sulfide).

A conductive cushion or conductive rubber compression pad 78 is located in the housing above the first current collector 69. A resistor plate 80 may be provided above pad 78. A battery 82 is placed above plate 80. The entire assembly or stack of components is maintained in compression by means of a pin 84 inserted across the upper end of the battery. An insulating plastic pull tab 85 or the like may be provided under the pin 84 for starting operation of the delivery system.

In this assembly, the electrodes (not illustrated) may be formed on the inner faces of porous discs 69, 70, which are surface-etched and platinum black activated, and then compressed against membrane 68. The second current collector 70 is in conductive contact with the outer housing, and the housing acts as an extension of the anodic current collector, connecting the anode or electrode formed on disc 70 to one end of the battery via metal pin 84. The opposite end of the battery is connected directly to an integral electrode or cathode on current collector 69 via resistor plate 80 and conductive pad 78. The first current collector is sealed from the conductive housing and second current collector by means of the projecting rim 72 of the membrane 68 in which it is housed, with the membrane material acting as the seal. This avoids the need for any separate sealing members or gaskets, since the membrane itself is used as the sealing material.

As in the first embodiment, this embodiment permits both electrodes to be connected to the battery on one side of the ion exchange membrane, and avoids the need for external wiring from the anode to the battery. In both of the above embodiments, the sealing forces are radial, rather than axial, providing independent sealing and contact directions to ensure continuing electrical contact during pressure induced deflections.

In the embodiments of FIGS. 1 to 5, the electrochemical cell has integral electrodes on opposite sides, formed by electro-catalytically active surfaces intimately attached to the membrane. However, in an alternative embodiment, the electrodes may be formed integrally with the current collectors shell end walls 12, 16. In this alternative, the current collector surfaces facing the membrane are electro-catalytically activated and forced into intimate contact with the membrane.

Although a preferred embodiment of the invention has been described above by way of example only, it will be understood by those skilled in the field that modifications may be made to the disclosed embodiment without departing form the scope of the invention, which is defined by the appended claims.

We claim:

1. An electrochemical cell module, comprising:

an outer shell of conductive material defining a cavity having a first, closed end and a second end facing in a first direction away from the first end;

an ion exchange membrane located in the cavity adjacent the first end of the cavity;

first and second pervious electrodes located on opposite sides of the membrane, the first electrode being located between the membrane and the first end of the cavity;

the first, closed end of the outer shell comprising a gas pervious current collector contacting the first electrode;

an inner shell of conductive material of shape substantially matching that of the outer shell, the inner shell having a first, closed end and a second open end and being nested inside the cavity formed by the outer shell in a parallel nesting arrangement with the second, open end of the inner shell facing in the same direction as the second end of the outer shell;

the first, closed end wall of the inner shell comprising a second, gas pervious current collector contacting the second electrode; and electrical contacts on the inner and outer shell on the same side of the module for connecting a power source across the electrodes.

2. The module as claimed in claim 1, wherein the outer shell comprises a cup-shaped member forming said cavity and having a closed first end wall having a plurality of openings and an open second end.

3. The module as claimed in claim 2, wherein the first end wall comprises a disc formed integrally with the outer shell.

4. The module as claimed in claim 2, wherein the inner shell is cup-shaped, the inner and outer shells each having a cylindrical wall and an end wall, the cylindrical walls of the shells defining an annular gap and a seal member comprising a ring-shaped seal located in said gap to seal the inner shell from the outer shell.

5. The module as claimed in claim 4, wherein the cylindrical wall of the outer shell and the ring seal are both of height greater than that of the cylindrical wall of the inner shell, and the second end of the outer shell is crimped inwardly over the open end of the inner shell with the seal having an end portion compressed between the crimped end of the outer shell and the end of the inner shell.

6. The module as claimed in claim 5, wherein the first end wall of the outer shell is dome-shaped in an unstressed condition and is deformed into a flat condition on crimping the second end of the outer shell over the inner shell, the deformed end wall of the outer shell comprising biasing means for biasing the end walls of the current collectors against said membrane.

7. The module as claimed in claim 2, wherein the end wall of the outer shell has a central portion extending across said first electrode, and an outer face with an annular groove extending around said central portion.

8. An electrochemical cell module, comprising:

an electrolytic membrane having opposite, first and second side faces;

first and second electrodes contacting the first and second side faces, respectively, of said electrolytic membrane;

a first current collector having a portion contacting the first electrode;

a second current collector having a portion contacting the second electrode; and a conductive outer shell extending from the first current collector and surrounding the electrolytic membrane, electrodes, and second current collector, the outer shell comprising an extension of said first current collector said outer shell is domed-shaped in an unstressed condition.

9. The module as claimed in claim 8, wherein the current collector portions contacting the respective electrodes are disc-shaped and each has a plurality of corrugations, the corrugations on one current collector portion extending at an angle to those on the other current collector portion.

10. The module as claimed in claim 9, wherein each current collector portion has a plurality of openings for gas flow to and from opposite sides of the electrolytic membrane.

11. The module as claimed in claim 10, wherein each current collector portion has a first corrugated face facing the electrolytic membrane, the first corrugated face comprising a plurality of troughs and peaks, each peak contacting the opposing face of the electrolytic membrane, and the openings being located at spaced intervals along each trough and spaced from the electrolytic membrane.

12. The module as claimed in claim 8, wherein the electrode-contacting portion of said first current collector comprises an end wall of said outer shell.

13. The module as claimed in claim 12, including an inner shell nested inside said outer shell and having an end wall comprising said electrode-contacting portion of said second current collector, the electrolytic membrane and electrodes being sandwiched between the end walls of said inner and outer shells.

14. The module as claimed in claim 13, including a seal member between said inner and outer shells.

15. The module as claimed in claim 8, wherein the outer shell comprises a housing having a through bore of stepped diameter, the through bore having a first stepped portion and a second stepped portion of larger diameter than the first stepped portion, the first current collector comprising a disc press fit into said first stepped portion, the membrane comprising a cup shaped member having a flat face contacting said first electrode and a second, recessed face containing said second electrode and said second current collector, the membrane and second current collector being a press fit in said second stepped portion, and said membrane insulating said second current collector from said conductive housing.

* * * * *